US011971416B2

(12) United States Patent
Kei et al.

(10) Patent No.: US 11,971,416 B2
(45) Date of Patent: Apr. 30, 2024

(54) ANALYSIS APPARATUS

(71) Applicants: YOKOGAWA ELECTRIC CORPORATION, Musashino (JP); University of Zurich, Zurich (CH)

(72) Inventors: Takayuki Kei, Musashino (JP); Yohei Tsubouchi, Musashino (JP); Lucas Pelkmans, Zurich (CH); Gabriele Gut, Zurich (CH)

(73) Assignees: YOKOGAWA ELECTRIC CORPORATION, Musashino (JP); University of Zurich, Zurich (CH)

( * ) Notice: Subject to any disclaimer, the term of this patent is extended or adjusted under 35 U.S.C. 154(b) by 160 days.

(21) Appl. No.: 17/342,542

(22) Filed: Jun. 9, 2021

(65) Prior Publication Data

US 2021/0382062 A1    Dec. 9, 2021

(30) Foreign Application Priority Data

Jun. 9, 2020    (JP) .................................. 2020-100405

(51) Int. Cl.
*G01N 33/58*    (2006.01)
*G01N 1/30*    (2006.01)

(52) U.S. Cl.
CPC ............. *G01N 33/582* (2013.01); *G01N 1/30* (2013.01)

(58) Field of Classification Search
CPC .... G01N 33/4875; G01N 35/10; H01R 12/71; H01R 2201/12
See application file for complete search history.

(56) References Cited

U.S. PATENT DOCUMENTS

| 2004/0033163 A1* | 2/2004 | Tseung ................. B65D 1/0223 422/63 |
| 2010/0028978 A1 | 2/2010 | Angros |
| 2019/0195756 A1 | 6/2019 | Aoki et al. |
| 2019/0376988 A1 | 12/2019 | Barnett et al. |
| 2022/0050122 A1* | 2/2022 | Imaeda .................. G01N 35/04 |

FOREIGN PATENT DOCUMENTS

| JP | H10123027 A | 5/1998 |
| WO | 2019207004 A1 | 10/2019 |

* cited by examiner

*Primary Examiner* — Jennifer Wecker
*Assistant Examiner* — Ali Husain Faraz
(74) *Attorney, Agent, or Firm* — KENJA IP LAW PC

(57) ABSTRACT

An analysis apparatus (1) includes a housing unit (10) that houses a biological sample (S), a staining dispenser unit (20) that fluorescently stains the biological sample (S), an image acquisition unit (30) that acquires an image of the biological sample (S), a washer unit (40) that destains the biological sample (S), a drive unit (50), and a control unit (90) that analyzes the image and controls the drive unit (50). The control unit (90) performs adjustments so that the staining dispenser unit (20) and the housing unit (10) satisfy a first position condition, performs adjustments so that the image acquisition unit (30) and the housing unit (10) satisfy a second position condition, and performs adjustments so that the washer unit (40) and the housing unit (10) satisfy a third position condition. The analysis apparatus (1) maximizes the actual photography range of information related to the biological sample. The analysis apparatus (1) can also minimize variation in the time required for processes and can achieve high-quality analysis.

5 Claims, 4 Drawing Sheets

ANALYSIS APPARATUS

CROSS-REFERENCE TO RELATED APPLICATION

The present application claims priority to Japanese Patent Application No. 2020-100405 filed Jun. 9, 2020, the entire contents of which are incorporated herein by reference.

TECHNICAL FIELD

The present disclosure relates to an analysis apparatus.

BACKGROUND

Techniques for comprehensively acquiring information of proteins in cells and performing function analysis and the like on the proteins are known. For example, patent literature (PTL) 1 discloses a multiplex staining method for biological samples in which a cycle formed by three processes, i.e. fluorescent staining, fluorescent imaging, and destaining, is repeated by multiplexing the cycle. In the multiplex staining method disclosed in PTL 1, the three processes in the cycle are each performed using a dedicated commercially-available device.

CITATION LIST

Patent Literature

PTL 1: WO2019/207004

SUMMARY

An analysis apparatus according to an embodiment is an analysis apparatus to be used in analysis of information related to a biological sample, the analysis apparatus including a housing unit configured to house the biological sample; a staining dispenser unit configured to fluorescently stain the biological sample housed in the housing unit; an image acquisition unit configured to acquire an image of the biological sample fluorescently stained by the staining dispenser unit; a washer unit configured to destain the biological sample fluorescently stained by the staining dispenser unit; a drive unit configured to drive at least one of the housing unit, the staining dispenser unit, the image acquisition unit, and the washer unit; and a control unit configured to analyze the image acquired by the image acquisition unit and to control the drive unit. The control unit is configured to perform adjustments so that the staining dispenser unit and the housing unit satisfy a first position condition, perform adjustments so that the image acquisition unit and the housing unit satisfy a second position condition, and perform adjustments so that the washer unit and the housing unit satisfy a third position condition.

DETAILED DESCRIPTION

Figure 1:
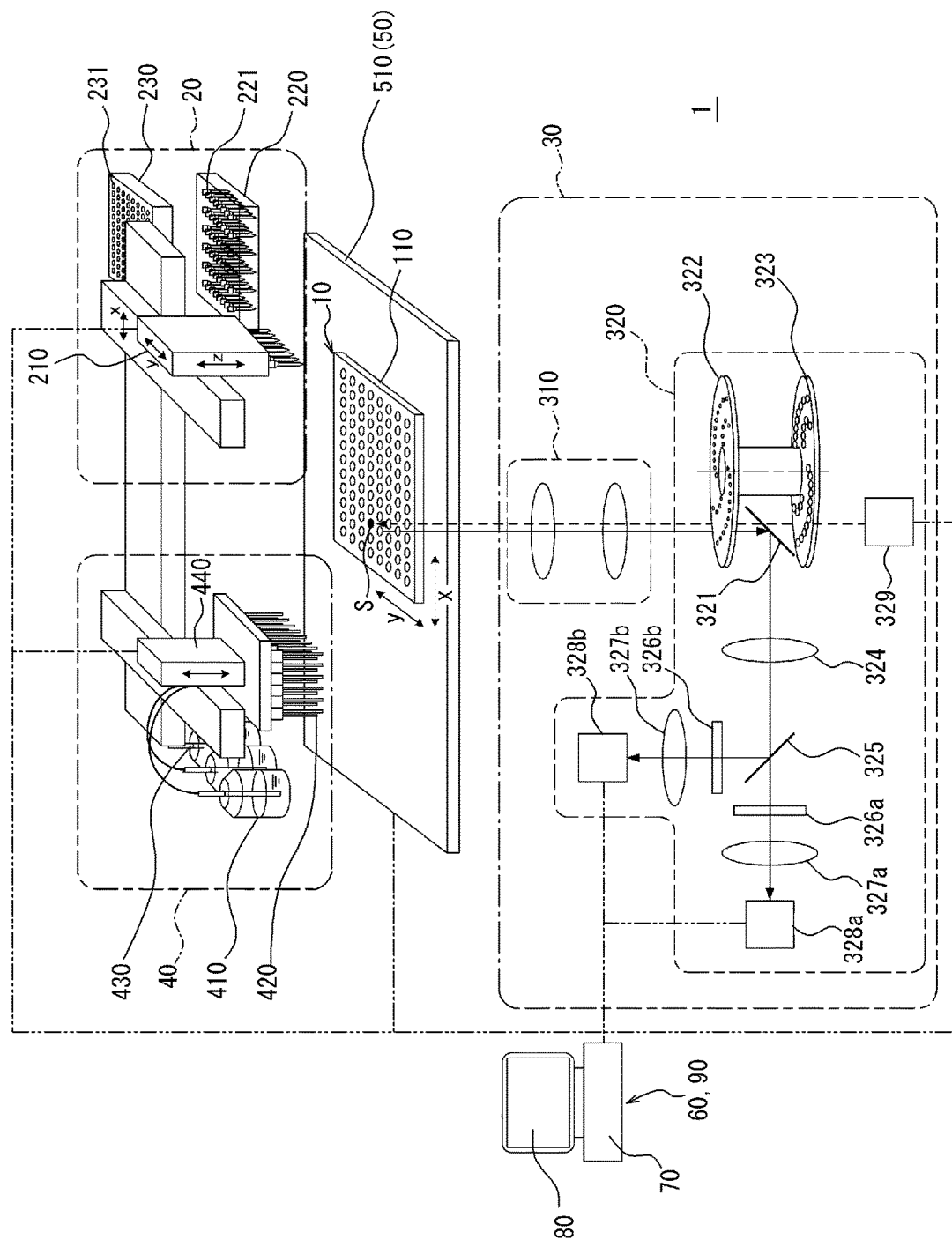
FIG. 1 schematically illustrates the configuration of an analysis apparatus according to an embodiment of the present disclosure.

Since the three processes of fluorescent staining, fluorescent imaging, and destaining are performed using three different dedicated commercially-available devices in the method disclosed in PTL 1, the microplate housing the biological sample needs to be extracted from one commercially-available device and placed in another commercially-available device between processes. When the microplate is placed in the commercially-available devices again during each repeated cycle, the position of the microplate in one commercially-available device shifts between cycles. This shift in position causes the photography range to be misaligned when photographing with a photography apparatus, such as a microscope used in fluorescent imaging. The actual photography range therefore becomes narrower. The time required for the processes also greatly varies.

The present disclosure aims to maximize the actual photography range of information related to a biological sample. The present disclosure can also minimize variation in the time required for processes and achieve high-quality analysis.

An analysis apparatus according to an embodiment is an analysis apparatus to be used in analysis of information related to a biological sample, the analysis apparatus including a housing unit configured to house the biological sample; a staining dispenser unit configured to fluorescently stain the biological sample housed in the housing unit; an image acquisition unit configured to acquire an image of the biological sample fluorescently stained by the staining dispenser unit; a washer unit configured to destain the biological sample fluorescently stained by the staining dispenser unit; a drive unit configured to drive at least one of the housing unit, the staining dispenser unit, the image acquisition unit, and the washer unit; and a control unit configured to analyze the image acquired by the image acquisition unit and to control the drive unit. The control unit is configured to perform adjustments so that the staining dispenser unit and the housing unit satisfy a first position condition, perform adjustments so that the image acquisition unit and the housing unit satisfy a second position condition, and perform adjustments so that the washer unit and the housing unit satisfy a third position condition.

As a result, the accuracy of analysis of information related to a biological sample improves. For example, the analysis apparatus integrally includes the staining dispenser unit, the image acquisition unit, and the washer unit and completes a cycle including the processes of fluorescent dying, fluorescent imaging, and destaining within a single apparatus. In greater detail, by the three units necessary in a multiplex staining method being incorporated in one apparatus, the analysis apparatus can execute the three processes of fluorescent staining, fluorescent imaging, and destaining while a microplate is held by an XY stage, without the need for removal from the XY stage. A sample container therefore need not be transferred between processes, as in a conventional technique, thereby improving the throughput of experiments. Additionally, the actual photography range of information related to a biological sample is maximized. Variation in the time required for the processes is also minimized. This enables high-quality analysis.

In an analysis apparatus according to an embodiment, the housing unit may be configured to move. As a result, the analysis apparatus enables each process to be executed while fixing the positions of the staining dispenser unit, the image acquisition unit, and the washer unit. By moving only the housing unit between processes, for example, the analysis apparatus can smoothly arrange the microplate held on the XY stage at positions based on each position condition. The throughput of experiments thereby improves.

In an analysis apparatus according to an embodiment, the control unit may be configured to control the drive unit in the order of the first position condition, the second position condition, and the third position condition. The analysis apparatus can thereby accurately execute the processes of fluorescent staining, fluorescent imaging, and destaining in order.

In an analysis apparatus according to an embodiment, the control unit may be configured to control the drive unit in the order of the first position condition and the third position condition. The analysis apparatus can thereby execute the process of fluorescent staining by the staining dispenser unit while removing, with the washer unit, excess chemicals included in a reagent other than the chemicals directly related to fluorescent staining. This improves the accuracy of fluorescent staining. Additionally, the analysis apparatus can execute the two processes of fluorescent staining and washing while the microplate is held by the XY stage, without the need for removal from the XY stage. A sample container therefore need not be transferred between processes, as in a conventional technique, thereby improving the throughput of experiments.

In an analysis apparatus according to an embodiment, the image acquisition unit may be configured to acquire a digital phase-contrast image of the biological sample using bright field illumination. With this configuration, the analysis apparatus can identify the biological sample using the digital phase-contrast image and therefore does not need to stain the nucleus of the biological sample with the staining dispenser unit. The image acquisition unit can allocate the fluorescent channel used for identifying the nucleus of the biological sample to identification of proteins included in the biological sample. Consequently, the experiment efficiency increases.

In an analysis apparatus according to an embodiment, the housing unit may be disposed on an XY stage. The housing unit thereby becomes capable of movement in the two XY directions.

In an analysis apparatus according to an embodiment, the housing unit may be disposed on a drive mechanism that enables movement in three XYZ directions. The housing unit thereby becomes capable of movement in the three XYZ directions.

In an analysis apparatus according to an embodiment, the washer unit may include a drive mechanism enabling movement in the Z-direction and may be connected to the drive mechanism of the housing unit. The washer unit is thereby capable of moving any structure included in the washer unit, such as washer heads, in the Z-direction using the drive mechanism. Additionally, connection of the washer unit to the drive mechanism of the housing unit enables movement of the washer unit in the three XYZ directions along with the housing unit.

The present disclosure maximizes the actual photography range of information related to a biological sample. The present disclosure can also minimize variation in the time required for processes and achieve high-quality analysis.

The background and problems with conventional techniques are described in greater detail.

In a conventional multiplex staining method, many types of proteins that carry out various functions inside cells are fluorescently stained several types at a time and are then subjected to fluorescent imaging under a microscope. The proteins in the fluorescently stained cells are then destained. Subsequently, several other types of proteins are then fluorescently stained, subjected to fluorescent imaging under a microscope, and destained. In this way, the processes of fluorescent staining, fluorescent imaging, and destaining of several types of proteins are repeated for all of the many types of proteins found in cells.

Based on the fluorescent image obtained by a multiplex staining method, the information of several tens of types, such as 40 types or more, of proteins can be comprehensively acquired. Such comprehensive information can be applied to function analysis of proteins, pathological diagnosis research, drug discovery research, and the like. Furthermore, such comprehensive information enables comprehensive cell profiling of pathological sections for understanding and explaining the origin of individual diseases. Multiplex staining methods are a technique ultimately leading to individualized medicine, precision medicine, and the like.

As described above, three processes are carried out in three different commercially-available devices in the method disclosed in PTL 1. This makes it necessary to remove a microplate, which is a cell container, from the commercially-available device used in one process and place the microplate in another commercially-available device used in the next process. When the microplate is placed in the commercially-available devices again during each repeated cycle, the position of the microplate in one commercially-available device shifts between cycles due to the microplate being transferred.

For example, during the fluorescent imaging process, such a shift in position leads to a difference in the photography range, i.e. the field of view, when photographing with a microscope. Such a difference in the photography range, i.e. the field of view, is a major problem and causes the cells observed during one cycle at a predetermined position in the microplate to differ from the cells observed in the next cycle. This makes it difficult to accurately analyze the relationship between proteins in individual cells and their interaction.

PTL 1 also discloses a method in which an image is trimmed by a photography apparatus to address the difference in the field of view. For example, when there is a difference of dx, dy in two orthogonal directions between a photography range that is a rectangular region in one cycle and a photography range that is a rectangular region in another cycle, the common portion between the photography ranges after all cycles are performed is outputted as a final common image. At this time, the images in other cycles are offset by image processing that corrects misalignment using the image in one cycle as a reference, for example.

In a trimming method such as the one in PTL 1, however, the biological sample is not used effectively, since information included in a range outside of the common portion of the photography range is left out from the final common image. In other words, the actual photography range becomes narrower in such a trimming method. The biological sample is consequently wasted, and costs increase. The time required for the processes also greatly varies.

To resolve these problems, the present disclosure aims to maximize the actual photography range of information related to a biological sample. The present disclosure can also minimize variation in the time required for processes and achieve high-quality analysis. Furthermore, the present disclosure aims to provide an analysis apparatus with improved analysis accuracy. The present disclosure additionally aims to provide an analysis apparatus that enables effective use of a biological sample and enables a reduction in costs.

In the present disclosure, a "biological sample" includes cells or the like cultured in each well of a microplate, for example. In the embodiments below, the biological sample is described as being limited to cells. This example is not limiting, however, and the biological sample may include tissue. In the present disclosure, the "information related to a biological sample" includes, for example, information of the proteins included in one cell; information of organelles including the cell nucleus, cytoplasm, mitochondria, or the like; information of the relationship between a plurality of cells; and the like. The "information of proteins" includes, for example, the form of each of the countless proteins included in one cell, the positional relationship between proteins, the relationship between functions and the like, and the interactional relationship.

To achieve these aims, an analysis apparatus according to an embodiment of the present disclosure integrally includes the below-described staining dispenser unit, image acquisition unit, and washer unit and completes a cycle including the processes of fluorescent staining, fluorescent imaging, and destaining within a single apparatus. The analysis apparatus is used in the analysis of information related to a biological sample, such as information of proteins.

The configuration and operations of an analysis apparatus according to an embodiment of the present disclosure are mainly described below with reference to the drawings.

FIG. 1 schematically illustrates the configuration of an analysis apparatus 1 according to an embodiment of the present disclosure. The configuration of the analysis apparatus 1 according to an embodiment of the present disclosure is mainly described with reference to FIG. 1.

A housing unit 10 houses cells S. As also illustrated in FIG. 1, the housing unit 10 includes a microplate 110 that houses the cells S in a plurality of wells. For example, the microplate 110 has 96 or 384 wells. The housing unit 10 is not limited to this configuration and may include any other sample container capable of housing cells S instead of or in addition to the microplate 110. For example, the housing unit 10 may include a cell culture container such as a cell culture dish, a cover glass chamber, a petri dish, or the like.

A staining dispenser unit 20 fluorescently stains the cells S housed in the housing unit 10. For example, the staining dispenser unit 20 fluorescently stains proteins in the cells S. The fluorescent staining is also carried out using a washer unit 40 in addition to the staining dispenser unit 20, as described below in FIG. 3. The staining dispenser unit 20 includes a multiple dispenser that has a fluorescent staining function. The staining dispenser unit 20 includes a drive mechanism 210 capable of moving the multiple dispenser in the three XYZ directions, for example. The multiple dispenser mounts tips 221 in a tip rack 220 onto multiple nozzles, such as 8 nozzles, and suctions a reagent 231 that includes antibodies or the like from a reagent rack 230. Subsequently, the multiple dispenser drips a predetermined liquid amount of the reagent 231 in each well of the microplate 110. The staining dispenser unit 20 thereby performs antibody staining on the cells S housed in each well of the microplate 110.

The image acquisition unit 30 acquires an image of the cells S fluorescently stained by the staining dispenser unit 20. The image acquisition unit 30 includes a laser confocal microscope, for example. The image acquisition unit 30 captures images of the cells S housed in the microplate 110 in order, well by well, with the laser confocal microscope.

The image acquisition unit 30 includes a microscope 310 that has a plurality of lenses and a confocal imaging unit 320.

The confocal imaging unit 320 includes a dichroic mirror 321, a pinhole array disc 322, a microlens array disc 323, and a relay lens 324. The confocal imaging unit 320 includes a dichroic mirror 325, a first bandpass filter 326a, a first lens 327a, a first camera 328a for fluorescence observation, a second bandpass filter 326b, a second lens 327b, and a second camera 328b for fluorescence observation. The confocal imaging unit 320 includes an excitation light source 329.

During fluorescence observation, the excitation light source 329 irradiates the microplate 110 with excitation light that has a specific wavelength. The sample that is excited among the cells S housed in the wells of the microplate 110 emits fluorescent light with a longer wavelength than the excitation light, for example. A confocal image is formed based on the fluorescent light that passes through the pinhole array disc 322. The florescent light is reflected by the dichroic mirror 321, passes through the relay lens 324, and forms an image on the first camera 328a for fluorescence observation and the second camera 328b for fluorescence observation.

The dichroic mirror 325 has optical characteristics that disperse fluorescent light and is arranged to support the simultaneous use of excitation light with multiple wavelengths. The first bandpass filter 326a and the second bandpass filter 326b have wavelength bands corresponding to the wavelength band of the fluorescent light and are arranged so as to increase the S/N ratio of the image. Various wavelength bands of fluorescent light are emitted by the cells S, and filter foil or the like may be used to arrange a plurality of bandpass filters corresponding to the required wavelength bands.

In FIG. 1, the image acquisition unit 30 includes one dichroic mirror 325 positioned towards the cameras for fluorescence observation from the relay lens 324 and has two sets of a bandpass filter, lens, and a camera for fluorescence observation, but this configuration is not limiting. The image acquisition unit 30 is not limited to such an optical system supporting two colors and may include an optical system supporting three or more colors. In this case, the image acquisition unit 30 may include two or more dichroic mirrors positioned towards the cameras for fluorescence observation from the relay lens 324 and have three or more sets of a bandpass filter, lens, and a camera for fluorescence observation.

The washer unit 40 destains the cells S fluorescently stained by the staining dispenser unit 20. The washer unit 40 includes a washer solution 410 that contains phosphate buffered saline (PBS), nuclease-free water (ddH$_2$O), imaging buffer solution (IB), or the like. The washer unit 40 includes washer heads 420 corresponding to the microplate 110 that has 96 wells, as illustrated in FIG. 1, or 384 wells. The washer solution 410 is supplied to the washer heads 420. The washer unit 40 includes a waste liquid bottle 430 into which waste liquid is discharged after washing. The washer unit 40 includes a drive mechanism 440 capable of moving the washer head 420 vertically (in the Z-direction), for example. A fluorescent reagent, for example, is eluted from the cells S by washing with the washer unit 40 and is discarded along with the washer solution 410.

The drive mechanism 210 of the staining dispenser unit 20 and the drive mechanism 440 of the washer unit 40 are connected to rails arranged in the X-direction in FIG. 1.

A drive unit 50 drives at least one of the housing unit 10, the staining dispenser unit 20, the image acquisition unit 30, and the washer unit 40. In the present disclosure, "at least one of A, B, and C" includes not only A, B, and C individually, but also any combination thereof. As illustrated in FIG. 1, the drive unit 50 includes an XY stage 510 that can move the housing unit 10 in the XY-directions, for example. However, this example is not limiting. The drive unit 50 may further include any stage capable of moving at least one of the staining dispenser unit 20, the image acquisition unit 30, and the washer unit 40.

A storage 60, an input unit 70, an output unit 80, and a control unit 90 are included in an information processing device, for example. Such an information processing device controls the staining dispenser unit 20, the image acquisition unit 30, the washer unit 40, and the drive unit 50, which are the other components of the analysis apparatus 1, for example. The information processing device includes any general-purpose electronic device, such as a personal computer (PC) communicatively connected to the other components of the analysis apparatus 1. This information processing device may be integrated into the analysis apparatus 1 or provided separately from the other components of the analysis apparatus 1. However, this example is not limiting. The information processing device may be one server or a plurality of communicatively connected servers, or may be a dedicated electronic device for the analysis apparatus 1. The storage 60, the input unit 70, the output unit 80, and the control unit 90 are not limited to being included together in one device, as described above, and may each independently form a portion of the analysis apparatus 1.

The storage 60 includes any storage module, such as a hard disk drive (HDD), a solid state drive (SSD), an electrically erasable programmable read-only memory (EEPROM), a read-only memory (ROM), and a random access memory (RAM). The storage 60 may, for example, function as a main storage apparatus, an auxiliary storage apparatus, or a cache memory. The storage 60 stores any information used in operations of the analysis apparatus 1. For example, the storage 60 may store system programs, application programs, various information received by communication, and the like. The storage 60 is not limited to being internal to the information processing device and may be an external database or an external storage module connected through a digital input/output port or the like, such as a universal serial bus (USB).

The input unit 70 includes an input interface that receives a user input operation and acquires one or more pieces of input information based on the user operation. For example, the input unit 70 may be a physical key, a capacitance key, a touchscreen provided integrally with the display of the output unit 80, a microphone that receives audio input, or the like, but these examples are not limiting.

The output unit 80 includes one or more output interfaces that output information to the user. For example, the output unit 80 may be a display that outputs information as images, a speaker that outputs information as sound, or the like, but these examples are not limiting. At least one of the input unit 70 and the output unit 80 may be formed integrally with the information processing device or formed separately.

The control unit 90 includes one or more processors. The "processor" in an embodiment is a general-purpose processor or a dedicated processor specialized for particular processing, but these examples are not limiting. The control unit 90 is communicatively connected with predetermined components of the analysis apparatus 1 and controls overall operations of the analysis apparatus 1.

The control unit 90 acquires setting conditions for the fluorescent staining, fluorescent imaging, and destaining in one cycle in advance based on a user input operation provided with the input unit 70, for example. Additionally, the control unit 90 acquires the setting of the number of iterations of the cycle in advance based on a user input operation provided with the input unit 70, for example. The control unit 90 stores the setting of the number of iterations of the cycle acquired in advance in the storage 60.

The control unit 90 makes adjustments during the cycle so that the staining dispenser unit 20 and the housing unit 10 satisfy a first position condition. In greater detail, the control unit 90 uses the drive unit 50 during the cycle to adjust the position of at least one of the staining dispenser unit 20 and the housing unit 10 so that a first position condition of the housing unit 10 relative to the staining dispenser unit 20 is satisfied when the cells S are fluorescently stained by the staining dispenser unit 20. In the present disclosure, the "first position condition" includes the positional relationship between the housing unit 10 and the staining dispenser unit 20 when, for example, the reagent 231 is dripped in the wells of the microplate 110 by the multiple dispenser.

For example, the control unit 90 uses the drive unit 50 to adjust the position of at least the housing unit 10 so that the first position condition is satisfied. The staining dispenser unit 20 is fixed in place, whereas the housing unit 10 moves, for example. In greater detail, the control unit 90 uses the XY stage 510 of the drive unit 50 to adjust the position of the microplate 110 included in the housing unit 10. The housing unit 10 is transported by the XY stage 510 to a position where the first position condition is satisfied. In this way, the position of the staining dispenser unit 20 and the position of the microplate 110 of the housing unit 10 are aligned with each other.

The control unit 90 controls the staining dispenser unit 20 to execute the process of fluorescent staining of the cells S while the first position condition of the housing unit 10 relative to the staining dispenser unit 20 is satisfied. At this time, the control unit 90 executes the process of fluorescent staining of the cells S while controlling the washer unit 40 in addition to the staining dispenser unit 20. The control unit 90 controls the drive mechanism 210 included in the staining dispenser unit 20 to execute the process of fluorescent staining while moving the multiple dispenser in the three XYZ directions, for example.

The control unit 90 makes adjustments during the cycle so that the image acquisition unit 30 and the housing unit 10 satisfy a second position condition. In greater detail, the control unit 90 uses the drive unit 50 during the cycle to adjust the position of at least one of the image acquisition unit 30 and the housing unit 10 so that a second position condition of the housing unit 10 relative to the image acquisition unit 30 is satisfied when an image of the fluorescently stained cells S is acquired by the image acquisition unit 30. In the present disclosure, the "second position condition" includes the positional relationship between the housing unit 10 and the image acquisition unit 30 when, for example, images of the cells S housed in the microplate 110 are captured in order, well by well, with a laser confocal microscope.

For example, the control unit 90 uses the drive unit 50 to adjust the position of at least the housing unit 10 so that the second position condition is satisfied. The image acquisition unit 30 is fixed in place, whereas the housing unit 10 moves, for example. In greater detail, the control unit 90 uses the XY stage 510 of the drive unit 50 to adjust the position of the microplate 110 included in the housing unit 10. The housing unit 10 is transported by the XY stage 510 to a position where the second position condition is satisfied. In this way, the position of the image acquisition unit 30 and the position of the microplate 110 of the housing unit 10 are aligned with each other.

The control unit 90 controls the image acquisition unit 30 to execute the process of fluorescent imaging of the fluorescently stained cells S while the second position condition of the housing unit 10 relative to the image acquisition unit 30 is satisfied. The control unit 90 controls the excitation light source 329 included in the image acquisition unit 30, for example, to irradiate the microplate 110 with excitation light. For example, the control unit 90 acquires the images captured by the first camera 328a for fluorescence observation and the second camera 328b for fluorescence observation, included in the image acquisition unit 30. The control unit 90 acquires the images from these cameras. The control unit 90 stores data of the images acquired from the image acquisition unit 30 in the storage 60, for example. The control unit 90 displays the images acquired from the image acquisition unit 30 on the output unit 80, for example.

The control unit 90 makes adjustments during the cycle so that the washer unit 40 and the housing unit 10 satisfy a third position condition. In greater detail, the control unit 90 uses the drive unit 50 during the cycle to adjust the position of at least one of the washer unit 40 and the housing unit 10 so that a third position condition of the housing unit 10 relative to the washer unit 40 is satisfied when the fluorescently stained cells S are destained by the washer unit 40. In the present disclosure, the "third position condition" includes the positional relationship between the housing unit 10 and the washer unit 40 when, for example, the wells of the microplate 110 are washed with the washer solution 410 by the washer heads 420.

For example, the control unit 90 uses the drive unit 50 to adjust the position of at least the housing unit 10 so that the third position condition is satisfied. The washer unit 40 is fixed in place, whereas the housing unit 10 moves, for example. In greater detail, the control unit 90 uses the XY stage 510 of the drive unit 50 to adjust the position of the microplate 110 included in the housing unit 10. The housing unit 10 is transported by the XY stage 510 to a position where the third position condition is satisfied. In this way, the position of the washer unit 40 and the position of the microplate 110 of the housing unit 10 are aligned with each other.

The control unit 90 controls the washer unit 40 to execute the process of destaining the fluorescently stained cells S while the third position condition of the housing unit 10 relative to the washer unit 40 is satisfied. The control unit 90 controls the drive mechanism 440 included in the washer unit 40 to move the washer heads 420 vertically, for example, thereby executing the destaining process.

The control unit 90 may control the drive unit 50 as described above in the order of the first position condition and the third position condition during the process of fluorescent staining, for example. The control unit 90 may control the drive unit 50 in the order of the first position condition, the second position condition, and the third position condition during a cycle, for example.

Subsequently, the control unit 90 judges whether the number of cycles has reached the number of iterations set in advance by the user using the input unit 70, for example. When judging that the number of iterations has not been reached, the control unit 90 repeats the cycle including the aforementioned fluorescent staining, fluorescent imaging, and destaining. When judging that the number of iterations has been reached, the control unit 90 comprehensively analyzes a plurality of images acquired by the image acquisition unit 30. In greater detail, the control unit 90 performs analysis on information of proteins and controls the drive unit 50, the drive mechanism 210, and the drive mechanism 440 based on the analysis of these images. The control unit 90 may output the analysis results to the output unit 80 as necessary.

Figure 2:
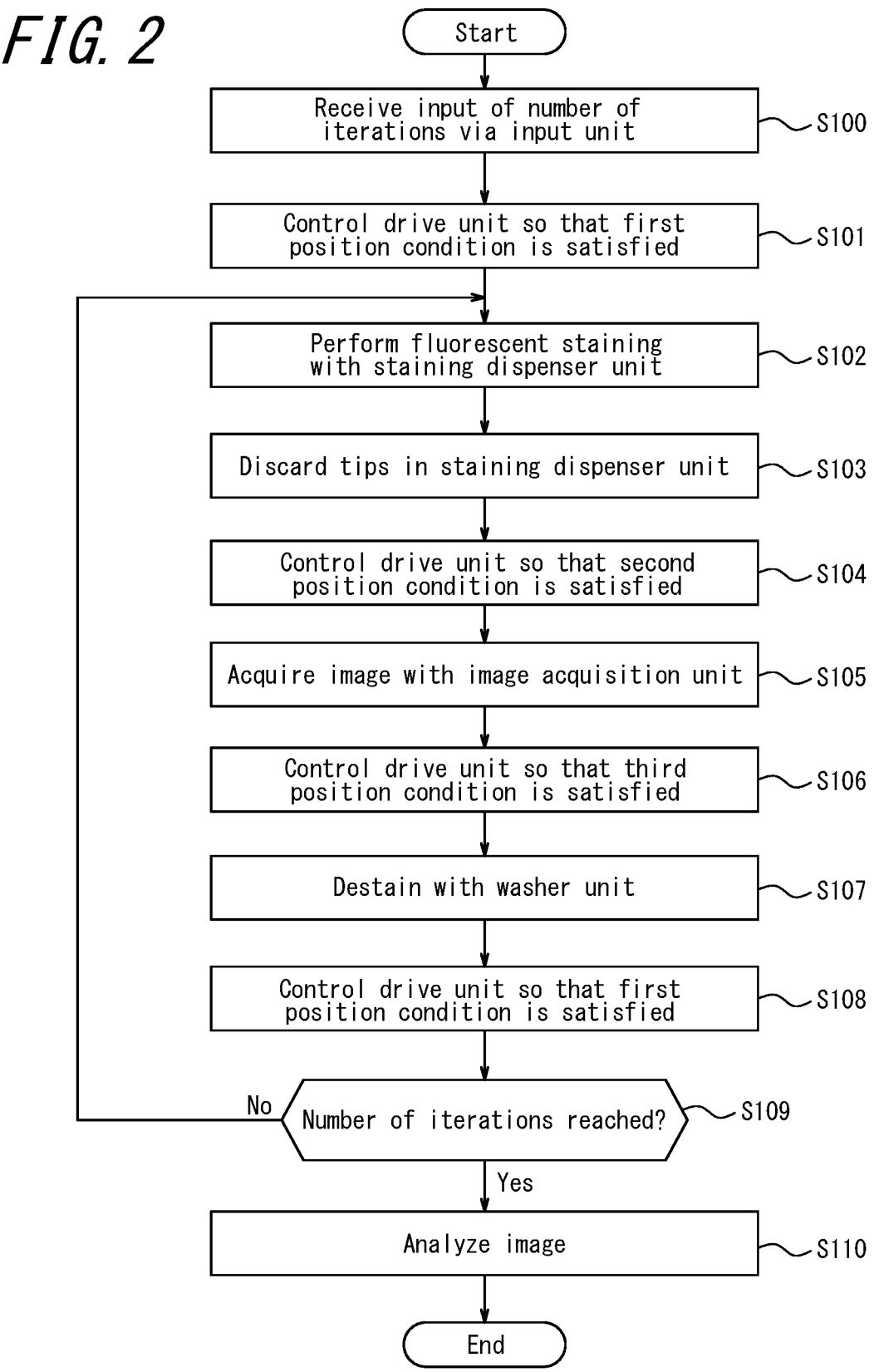
FIG. 2 is a flowchart illustrating a first example of operations executed by the analysis apparatus of FIG. 1.

FIG. 2 is a flowchart illustrating a first example of operations executed by the analysis apparatus 1 of FIG. 1. The first example of operations executed by the analysis apparatus 1 is mainly described with reference to FIG. 2. The explanation of the process of fluorescent staining is simplified in the first example of operations to explain the overall basic flow of a cycle. At this time, the control unit 90 controls the drive unit 50 in the order of the first position condition, the second position condition, and the third position condition during a cycle.

For example, a user first cultures cells S according to a predetermined protocol in the microplate 110. The user places the microplate 110 housing the cultured cells S on the XY stage 510 of the drive unit 50, for example.

In step S100, the control unit 90 of the analysis apparatus 1 receives, from the input unit 70, input of the number of iterations of the cycle of fluorescent staining, fluorescent imaging, and destaining based on a user input operation provided with the input unit 70, for example.

In step S101, the control unit 90 controls the drive unit 50 so that the first position condition of the housing unit 10 relative to the staining dispenser unit 20 is satisfied when the cells S are fluorescently stained by the staining dispenser unit 20. For example, the control unit 90 uses the drive unit 50 to adjust the position of the housing unit 10 so that the first position condition is satisfied. In greater detail, the XY stage 510 of the drive unit 50 transports the microplate 110 of the housing unit 10 to the position of the multiple dispenser of the staining dispenser unit 20 so that the first position condition is satisfied. The value of the first position condition stored in advance in the storage 60 is used for adjustment.

In step S102, the control unit 90 controls the staining dispenser unit 20 so that the staining dispenser unit 20 fluorescently stains the cells S housed in the housing unit 10. For example, the multiple dispenser of the staining dispenser unit 20 mounts the tips 221 in the tip rack 220 onto multiple nozzles, such as 8 nozzles, and suctions the reagent 231 that includes antibodies or the like from the reagent rack 230. Subsequently, the multiple dispenser drips a predetermined liquid amount of the reagent 231 in each well of the microplate 110. The staining dispenser unit 20 thereby performs primary antibody staining, secondary antibody staining, nuclear staining, and the like on the cells S housed in each well of the microplate 110.

In step S103, the control unit 90 controls the staining dispenser unit 20 to remove the tips 221 from the nozzles after completion of the fluorescent staining process of step S102 and to release the tips 221 into a predetermined container to discard the tips 221 in the staining dispenser unit 20.

In step S104, the control unit 90 controls the drive unit 50 so that the second position condition of the housing unit 10 relative to the image acquisition unit 30 is satisfied when an image of the cells S fluorescently stained in step S102 is acquired by the image acquisition unit 30. For example, the control unit 90 uses the drive unit 50 to adjust the position of the housing unit 10 so that the second position condition is satisfied. In greater detail, the XY stage 510 of the drive unit 50 transports the microplate 110 of the housing unit 10 to the photography position of the image acquisition unit 30 so that the second position condition is satisfied. The value of the second position condition stored in advance in the storage 60 is used for adjustment.

In step S105, the control unit 90 uses the image acquisition unit 30 to acquire images in order, well by well, of the cells S fluorescently stained in step S102. In other words, the control unit 90 executes the process of fluorescent imaging using the image acquisition unit 30.

In step S106, the control unit 90 controls the drive unit 50 so that the third position condition of the housing unit 10 relative to the washer unit 40 is satisfied when the cells S fluorescently stained in step S102 are destained by the washer unit 40. For example, the control unit 90 uses the drive unit 50 to adjust the position of the housing unit 10 so that the third position condition is satisfied. In greater detail, the XY stage 510 of the drive unit 50 transports the microplate 110 of the housing unit 10 to the position of destaining by the washer heads 420 of the washer unit 40 so that the third position condition is satisfied. The value of the third position condition stored in advance in the storage 60 is used for adjustment.

In step S107, the control unit 90 uses the washer unit 40 to destain the cells S fluorescently stained in step S102. For example, the washer unit 40 washes using the washer solution 410 while blocking to achieve antibody elution from the cells S.

In step S108, the control unit 90 controls the drive unit 50 so that the first position condition is satisfied, as in step S101.

In step S109, the control unit 90 judges whether the number of cycles of fluorescent staining, fluorescent imaging, and destaining has reached the number of iterations inputted by the user in step S100. The control unit 90 executes the processing of step S110 when judging that the number of iterations has been reached. The control unit 90 executes the processing of step S102 again when judging that the number of iterations has not been reached.

When the control unit 90 judges that the number of iterations has been reached in step S109, then in step S110, the control unit 90 analyzes the images acquired by the image acquisition unit 30. In greater detail, the control unit 90 analyzes information of proteins based on an analysis of the images acquired by the image acquisition unit 30.

Figure 3:
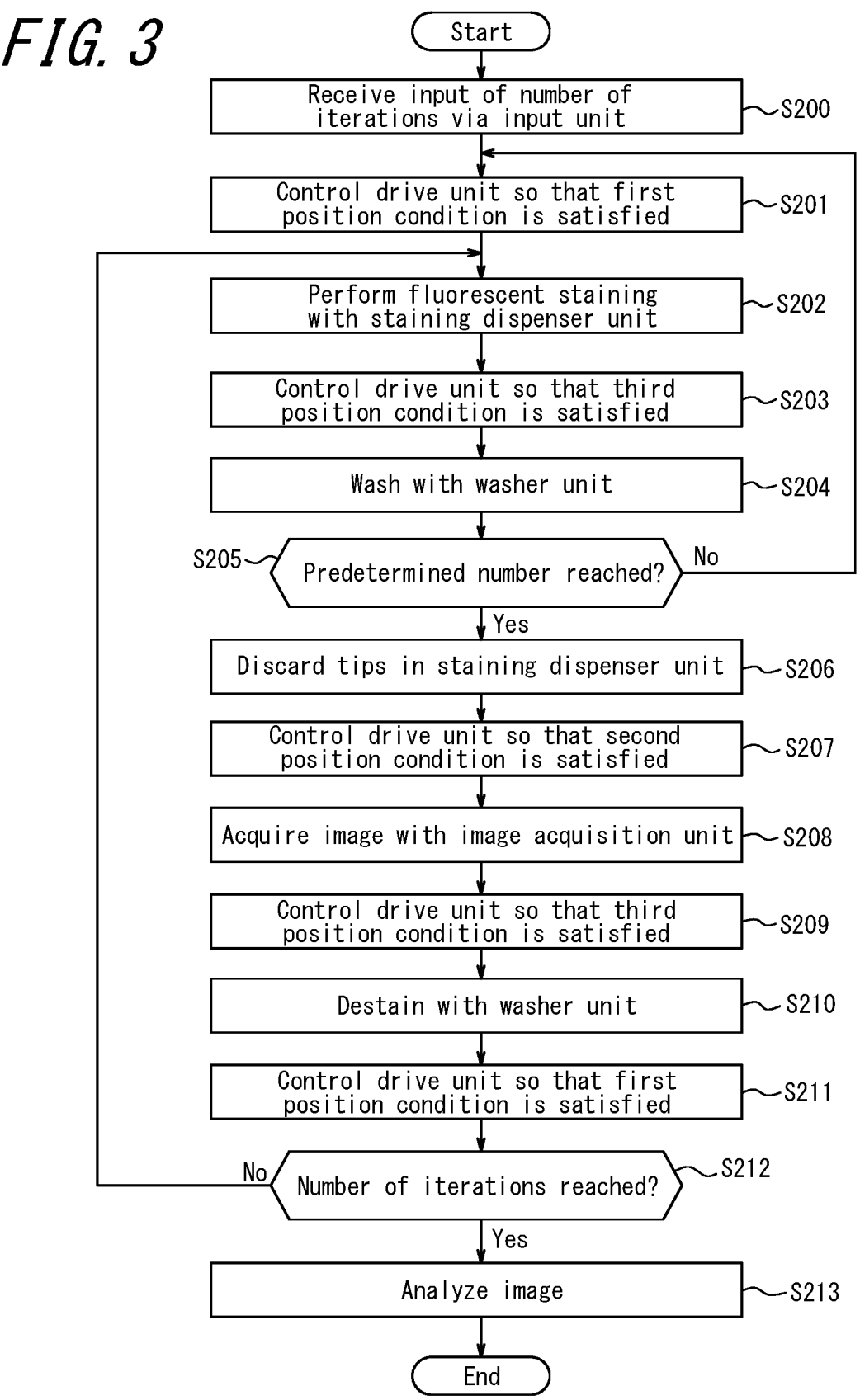
FIG. 3 is a flowchart illustrating a second example of operations executed by the analysis apparatus of FIG. 1.

FIG. 3 is a flowchart illustrating a second example of operations executed by the analysis apparatus 1 of FIG. 1. The second example of operations executed by the analysis apparatus 1 is mainly described with reference to FIG. 3. In the second example of operations, the process of fluorescent staining is described in detail. At this time, the control unit 90 controls the drive unit 50 in the order of the first position condition and the third position condition during the process of fluorescent staining. In other words, in addition to the aforementioned configuration for performing the processes of fluorescent staining, fluorescent imaging, and destaining in this order, the control unit 90 also includes a process of washing by the washer unit 40 after the fluorescent staining in the cycle.

The processing by the control unit 90 in steps S200 through S202 and S206 through S213 in FIG. 3 is the same as the processing of steps S100 through S110 in FIG. 2. A description of the processing of steps shared in common with FIG. 2 is omitted from the following description based on FIG. 3 so as to focus mainly on the processing of steps that differ from FIG. 2.

In step S203, the control unit 90 controls the drive unit 50 so that the third position condition is satisfied after completion of the process of fluorescent staining in step S202. For example, the control unit 90 uses the drive unit 50 to adjust the position of the housing unit 10 so that the third position condition is satisfied. In greater detail, the XY stage 510 of the drive unit 50 transports the microplate 110 of the housing unit 10 to the position of washing by the washer heads 420 of the washer unit 40 so that the third position condition is satisfied. The value of the third position condition stored in advance in the storage 60 is used for adjustment.

In step S204, the control unit 90 uses the washer unit 40 to destain the cells S fluorescently stained in step S202. At this time, the washer unit 40 does not remove the fluorescent color adhered to the proteins in the cells S by the fluorescent staining but rather removes excess chemicals included in the reagent 231 other than the chemicals directly related to fluorescent staining.

In step S205, the control unit 90 judges whether the number of cycles of fluorescent staining by the staining dispenser unit 20 and washing by the washer unit 40 has reached a predetermined number. The control unit 90 executes the processing of step S206 when judging that the predetermined number has been reached. The control unit 90 executes the processing of step S201 again when judging that the predetermined number has not been reached. In the present description, the "predetermined number" corresponds to the number of fluorescent colors used in fluorescent staining in one cycle of fluorescent staining, fluorescent imaging, and destaining, for example. When the number of fluorescent colors used in fluorescent staining is four, for example, the predetermined number is four.

The above-described analysis apparatus 1 according to an embodiment improves the accuracy of analysis of information related to a biological sample. For example, the analysis apparatus 1 integrally includes the staining dispenser unit 20, the image acquisition unit 30, and the washer unit 40 and completes a cycle including the processes of fluorescent staining, fluorescent imaging, and destaining within a single apparatus. In greater detail, by the three units necessary in a multiplex staining method being incorporated in one apparatus, the analysis apparatus 1 can execute the three processes of fluorescent staining, fluorescent imaging, and destaining while the microplate 110 is held by the XY stage 510, without the need for removal of the microplate 110 from the XY stage 510. A sample container therefore need not be transferred between processes, as in a conventional technique, thereby improving the throughput of experiments. In the present disclosure, the "throughput" includes the data capacity, speed, and the like, for example. Additionally, the actual photography range of information related to a biological sample is maximized. Variation in the time required for the processes is also minimized. This enables high-quality analysis.

Misalignment between cycles as a result of a sample container being removed from a commercially-available device and reinstalled as in a conventional technique, for example, therefore does not occur in the analysis apparatus 1. Accordingly, even when cycles are repeated, the analysis apparatus 1 is capable of accurately identifying the same cells S at the same position of the microplate 110 between cycles. The analysis apparatus 1 thereby also enables accurate analysis of information related to a biological sample.

When a sample container is inserted or removed from under a microscope in a conventional technique, the repeat accuracy of the removal mechanism is limited and has an error of several hundred micrometers. This error causes the range of photographs cells, i.e. the field of view, to change each time cells are photographed by the microscope, and proteins that are supposed to be in the same cell appear in different cells. Since the size of cells is several tens of micrometers or less, the error in the removal mechanism of the sample container is an order of magnitude greater than the cell size. It is therefore extremely important to improve the position accuracy of the sample container.

In the case of the analysis apparatus 1, the microplate 110 is continually held by the XY stage 510 while the entire cycle is repeated. Accordingly, misalignment of the microplate 110 occurring between cycles is 10 micrometers or less, for example approximately several micrometers. The misalignment in the case of the analysis apparatus 1 is therefore an order of magnitude smaller than the size of the cells S. Even when cycles are repeated, the same cell S at the same position of the microplate 110 can thus be disposed at substantially the same position relative to the image acquisition unit 30. The reproducibility of the position of the microplate 110 is extremely high between cycles in the analysis apparatus 1. Consequently, the field of view of the cells S photographed in each repeated cycle is constant. This highly accurate reproducibility of the position improves the reliability of experimental data and maintains high quality of the analysis results.

The above-described suppression of misalignment enables effective use of cells S in the analysis apparatus 1 and can reduce costs. For example, the problem of loss of information included in a range outside of the common portion of the photography range, as in a conventional technique, does not occur in the analysis apparatus 1, and the cells S can be used effectively. Additionally, the burden of image processing related to aligning the position of captured images between cycles is unnecessary, improving the experiment efficiency.

The housing unit 10 moves in the analysis apparatus 1, enabling each process to be executed while fixing the positions of the staining dispenser unit 20, the image acquisition unit 30, and the washer unit 40. By moving only the housing unit 10 between processes, for example, the analysis apparatus 1 can smoothly arrange the microplate 110 held on the XY stage 510 at positions satisfying each position condition. The throughput of experiments thereby improves.

The analysis apparatus 1 can accurately execute the processes of fluorescent staining, fluorescent imaging, and destaining in order by controlling the drive unit 50 in the order of the first position condition, the second position condition, and the third position condition.

By controlling the drive unit 50 in the order of the first position condition and the third position condition, the analysis apparatus 1 can execute the process of fluorescent staining by the staining dispenser unit 20 while removing, with the washer unit 40, excess chemicals included in the reagent 231 other than the chemicals directly related to fluorescent staining. This improves the accuracy of fluorescent staining. Additionally, the analysis apparatus 1 can execute the two processes of fluorescent staining and washing while the microplate 110 is held by the XY stage 510, without the need for removal of the microplate 110 from the XY stage 510. A sample container therefore need not be transferred between processes, as in a conventional technique, thereby improving the throughput of experiments.

The housing unit 10 can move in the two XY directions by virtue of being disposed on the XY stage 510.

The throughput of experiments is improved by the housing unit 10 including the microplate 110 that houses the cells S in a plurality of wells. In greater detail, the capacity of data obtained by experiment improves.

For example, with a conventional technique in which the cell container is a micro fluid chamber, cells are seeded in the micro fluid chamber. At this time, the micro flow path is limited in physical size, and the amount of seeded cells is also limited. Consequently, a low amount of information is obtained by experiment, and the throughput of experiments is low.

On the other hand, the microplate 110 is used as the sample container in the analysis apparatus 1 and includes 96 or 384 wells, for example, containing the cells S. The analysis apparatus 1 can thereby measure a large quantity of cells S and improve the throughput of experiments. Additionally, the resulting data capacity is overwhelmingly larger, improving the reliability of the analysis apparatus.

Although the present disclosure is based on embodiments and drawings, it is to be noted that various changes and modifications will be apparent to those skilled in the art based on the present disclosure. Therefore, such changes and modifications are to be understood as included within the scope of the present disclosure. For example, the functions and the like included in the components, steps, and the like may be reordered in any logically consistent way. Furthermore, components, steps, and the like may be combined into one or divided.

For example, the present disclosure may also be embodied as a program containing a description of the processing for achieving the functions of the above-described analysis apparatus 1 or a recording medium with the program recorded thereon. Such embodiments are also to be understood as falling within the scope of the present disclosure.

For example, the shape, arrangement, orientation, and number of the above-described components are not limited to the above explanation or the drawings. The shape, arrangement, orientation, and number of each component may be selected freely as long as the functions of the component can be achieved.

Figure 4:
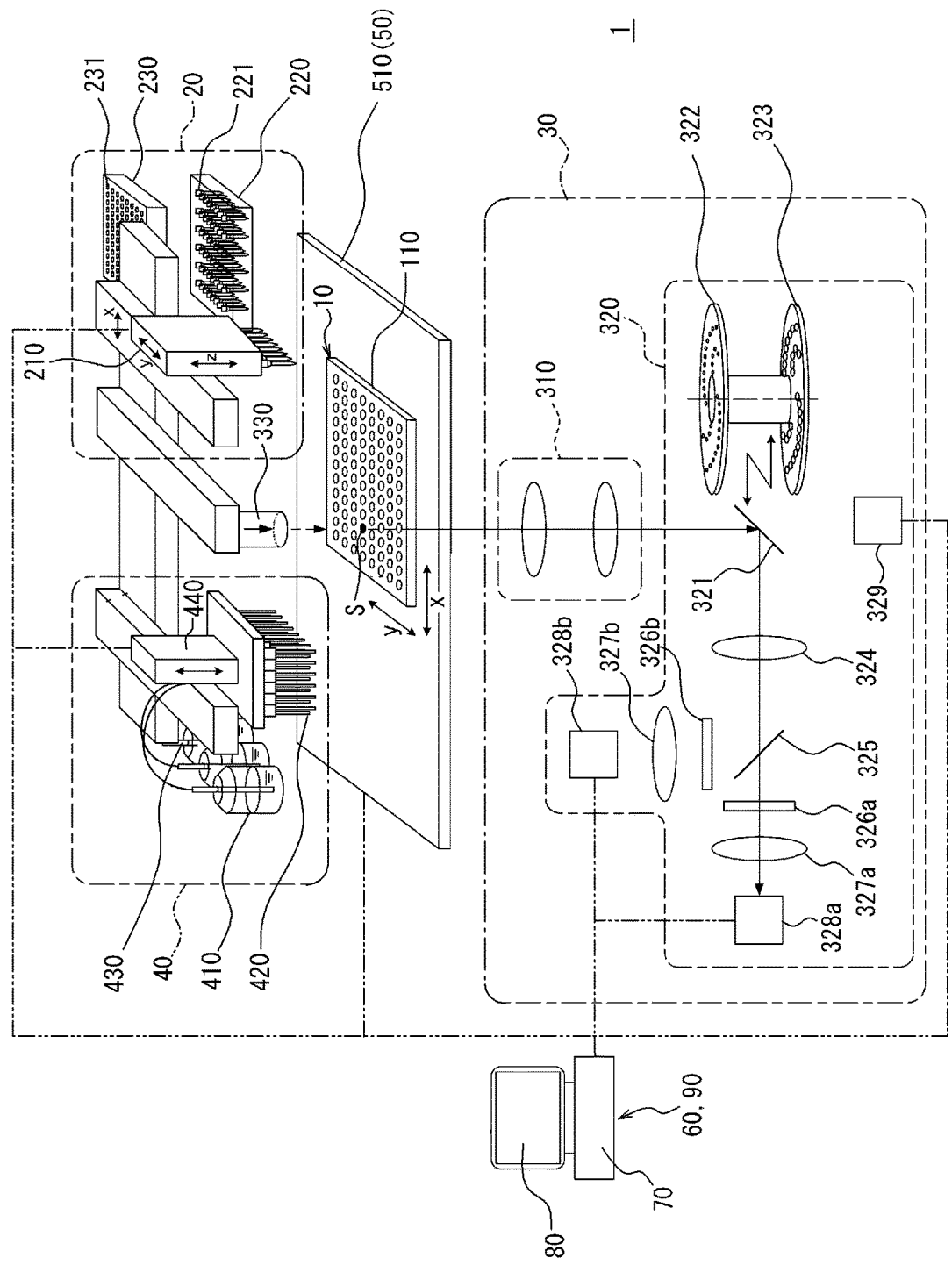
FIG. 4 schematically illustrates a modification to the analysis apparatus of FIG. 1.

FIG. 4 schematically illustrates a modification to the analysis apparatus of FIG. 1. With reference to FIG. 4, the modification to the analysis apparatus 1 is mainly described. The example in FIG. 1 and the example in FIG. 4 differ in that the example in FIG. 4 includes a bright field illumination unit 330, and the florescent light from the cells S is directly incident on the dichroic mirror 321 without passing through the pinhole array disc 322. The analysis apparatus 1 of the example in FIG. 4 includes means for moving the pinhole array disc 322 and the microlens array disc 323.

For example, the analysis apparatus 1 may further include the bright field illumination unit 330. At this time, the image acquisition unit 30 may use the bright field illumination unit 330 to acquire a digital phase-contrast image of the cells S. The bright field illumination unit 330 includes a light-emitting diode (LED), for example.

By contrast, the analysis apparatus 1 of the example in FIG. 1 normally performs identification, on the image obtained in each cycle during the fluorescent imaging process, using the nucleus of the cell S to judge whether the cell S is the same. The analysis apparatus 1 stains the nucleus of the cell S with the staining dispenser unit 20, identifies the nucleus of the cell S with fluorescent imaging, and identifies each cell S. Subsequently, the analysis apparatus 1 associates proteins with each cell S. The positional relationship is identified for images obtained in different cycles using an image of the nucleus of the cell S as a reference. The analysis apparatus 1 therefore needs to stain the nucleus of the cells S with the staining dispenser unit 20 each time the cycle is repeated. The analysis apparatus 1 photographs the nucleus of the cells S, stained by the staining dispenser unit 20, by fluorescent imaging in each cycle. One fluorescent channel in the image acquisition unit 30 therefore always needs to be allocated to the nucleus of the cell S.

The analysis apparatus 1 in the example in FIG. 4 acquires a digital phase-contrast image of the cell S and can thereby allocate the fluorescent channel to the protein being analyzed instead of the nucleus of the cell S. This enables the fluorescent imaging process to be executed efficiently in each cycle. For example, the image acquisition unit 30 irradiates cells S with the bright field illumination unit 330 and acquires a bright field image. Based on the acquired bright field image, for example, the image acquisition unit 30 generates a digital phase-contrast image of the nucleus of the cell S. The analysis apparatus 1 identifies the cell S based on the generated digital phase-contrast image.

The image acquisition unit 30 moves an object lens in the microscope 310 at predetermined intervals in the optical axis direction to two or three locations. The image acquisition unit 30 acquires bright field images while displacing the object lens at predetermined intervals and performs image processing on the two or three acquired bright field images. In this way, the image acquisition unit 30 generates a digital phase-contrast image.

The analysis apparatus 1 identifies the cells S using the digital phase-contrast image and therefore does not need to stain the nucleus of the cells S with the staining dispenser unit 20. Accordingly, the analysis apparatus 1 can efficiently perform fluorescent staining. The image acquisition unit 30 can also allocate the fluorescent channel used for identifying the nucleus of the cell S to identification of proteins included in the cell S. Consequently, the experiment efficiency increases.

The analysis apparatus 1 of the example in FIG. 4 can turn the bright field illumination unit 330 off and move the pinhole array disc 322 and the microlens array disc 323 to the positions of the example in FIG. 1 to execute a fluorescent imaging process similar to that of the example in FIG. 1. The analysis apparatus 1 of the example in FIG. 4 can achieve both acquisition of a digital phase-contrast image and fluorescent imaging with a simple configuration. Achievement of these functions with a simple configuration enables a reduction in size of the analysis apparatus 1. Additionally, this analysis apparatus 1 is capable of stable, high-quality operations.

In the above embodiment, the analysis apparatus 1 has been described as adjusting the position of the housing unit 10 using the drive unit 50 in each process, but this configuration is not limiting. For example, the analysis apparatus 1 may use the drive unit 50 to adjust the position of the staining dispenser unit 20, or the positions of both the staining dispenser unit 20 and the housing unit 10, so that the first position condition is satisfied in the fluorescent staining process. The analysis apparatus 1 may, for example, use the drive unit 50 to adjust the position of the image acquisition unit 30, or the positions of both the image acquisition unit 30 and the housing unit 10, so that the second position condition is satisfied in the fluorescent imaging process. The analysis apparatus 1 may, for example, use the drive unit 50 to adjust the position of the washer unit 40, or the positions of both the washer unit 40 and the housing unit 10, so that the third position condition is satisfied in the destaining process.

In the above embodiment, the housing unit 10 has been described as being disposed on the XY stage 510, but this configuration is not limiting. Instead of or in addition to the XY stage 510, the housing unit 10 may be disposed on a drive mechanism that enables movement in the three XYZ directions. The housing unit 10 thereby becomes capable of movement in the three XYZ directions.

For example, the washer unit 40 may include the above-described drive mechanism 440 that enables movement in the Z-direction and be connected to the drive mechanism of the housing unit 10. In greater detail, the washer unit 40 may be connected to the drive mechanism on which the housing unit 10 is disposed. The washer unit 40 is thereby capable of moving any structure included in the washer unit 40, such as the washer heads 420, in the Z-direction using the drive mechanism 440. Additionally, connection of the washer unit 40 to the drive mechanism of the housing unit 10 enables movement of the washer unit 40 in the three XYZ directions along with the housing unit 10.

The invention claimed is:

1. An analysis apparatus to be used in analysis of information related to a biological sample, the analysis apparatus comprising:
    a housing unit configured to house the biological sample, wherein the housing unit is disposed on a first drive mechanism, the first drive mechanism configured to enable movement in three XYZ directions;
    a staining dispenser unit, comprising a second drive mechanism, wherein the second drive mechanism is configured to move a multiple dispenser in the three XYZ directions, the multiple dispenser configured to fluorescently stain the biological sample housed in the housing unit;
    an image acquisition unit configured to acquire an image of the biological sample fluorescently stained by the staining dispenser unit;
    a washer unit, disposed separate from the staining dispenser unit, configured to destain the biological sample fluorescently stained by the staining dispenser unit, wherein the washer unit comprises a third drive mechanism configured to enable movement in the Z-direction, the third drive mechanism connected to the first drive mechanism of the housing unit;
    a drive unit configured to drive at least one of the housing unit, the staining dispenser unit, the image acquisition unit, and the washer unit; and
    a control unit configured to analyze the image acquired by the image acquisition unit and to control the drive unit;
    wherein the control unit is programmed to
        perform adjustments so that the staining dispenser unit and the housing unit satisfy a first position condition;
        control the third drive mechanism of the staining dispenser unit, in order to execute the process of fluorescent staining while moving the multiple dispenser in the three XYZ directions;
        perform adjustments so that the image acquisition unit and the housing unit satisfy a second position condition;
        perform adjustments so that the washer unit and the housing unit satisfy a third position condition; and
        control the staining dispenser unit, the image acquisition unit, and the washer unit so as to perform, separately, fluorescent staining by the staining dispenser unit, fluorescent imaging by the image acquisition unit, and destaining by the washer unit in a single cycle and repeat the cycle.

2. The analysis apparatus of claim 1, wherein the housing unit is configured to move.

3. The analysis apparatus of claim 1, wherein the control unit is configured to control the drive unit in the order of the first position condition, the second position condition, and the third position condition.

4. The analysis apparatus of claim 1, wherein the control unit is configured to control the drive unit in the order of the first position condition and the third position condition.

5. The analysis apparatus of claim 1, wherein the image acquisition unit is configured to acquire a digital phase-contrast image of the biological sample using bright field illumination.

* * * * *